United States Patent [19]
Walker et al.

[11] Patent Number: 5,397,311
[45] Date of Patent: Mar. 14, 1995

[54] BLOODLESS SPLITTABLE INTRODUCER

[75] Inventors: Jack M. Walker, Portola Valley; Daniel J. Balbierz, Sunnyvale; George Tsai, Sunnyvale, all of Calif.

[73] Assignee: Menlo Care, Inc., Menlo Park, Calif.

[21] Appl. No.: 942,724

[22] Filed: Sep. 9, 1992

[51] Int. Cl.[6] ............................................. A61M 5/178
[52] U.S. Cl. ..................................................... 604/160
[58] Field of Search ............... 604/164, 169, 171, 160, 604/280, 247, 246

[56] References Cited

U.S. PATENT DOCUMENTS

| | | | |
|---|---|---|---|
| 4,143,853 | 3/1979 | Abramson | 604/246 X |
| 4,776,846 | 10/1988 | Wells | 604/280 X |
| 5,009,391 | 4/1991 | Steigerwald | 604/247 X |
| 5,125,904 | 6/1992 | Lee | 604/164 |
| 5,154,701 | 10/1992 | Cheek et al. | 604/169 X |
| 5,167,634 | 12/1992 | Lorrigan, Jr. et al. | 604/164 X |
| 5,221,263 | 6/1993 | Sinko et al. | 604/164 X |

*Primary Examiner*—Gene Mancene
*Assistant Examiner*—Thomas Price
*Attorney, Agent, or Firm*—Fliesler, Dubb, Meyer & Lovejoy

[57] ABSTRACT

An apparatus is provided for facilitating substantially bloodless insertion into and withdrawal from a patient's body of a longitudinal member having a proximal end portion and having a distal end portion which is adapted to extend into the patient's body. The apparatus comprises a longitudinally extending sleeve having proximal and distal end portions and defining a lumen extending there along. The longitudinal member is positioned along the lumen. The sleeve has a line extending longitudinally along it which is either split or splittable so that the sleeve can be separated along the line for removal from about the longitudinal member while the distal end portion of the longitudinal member remains extended into the patient. A valve structure serves for preventing blood flow through the lumen. An access is present for allowing substantially bloodless insertion and withdrawal of the longitudinal member through the lumen.

3 Claims, 7 Drawing Sheets

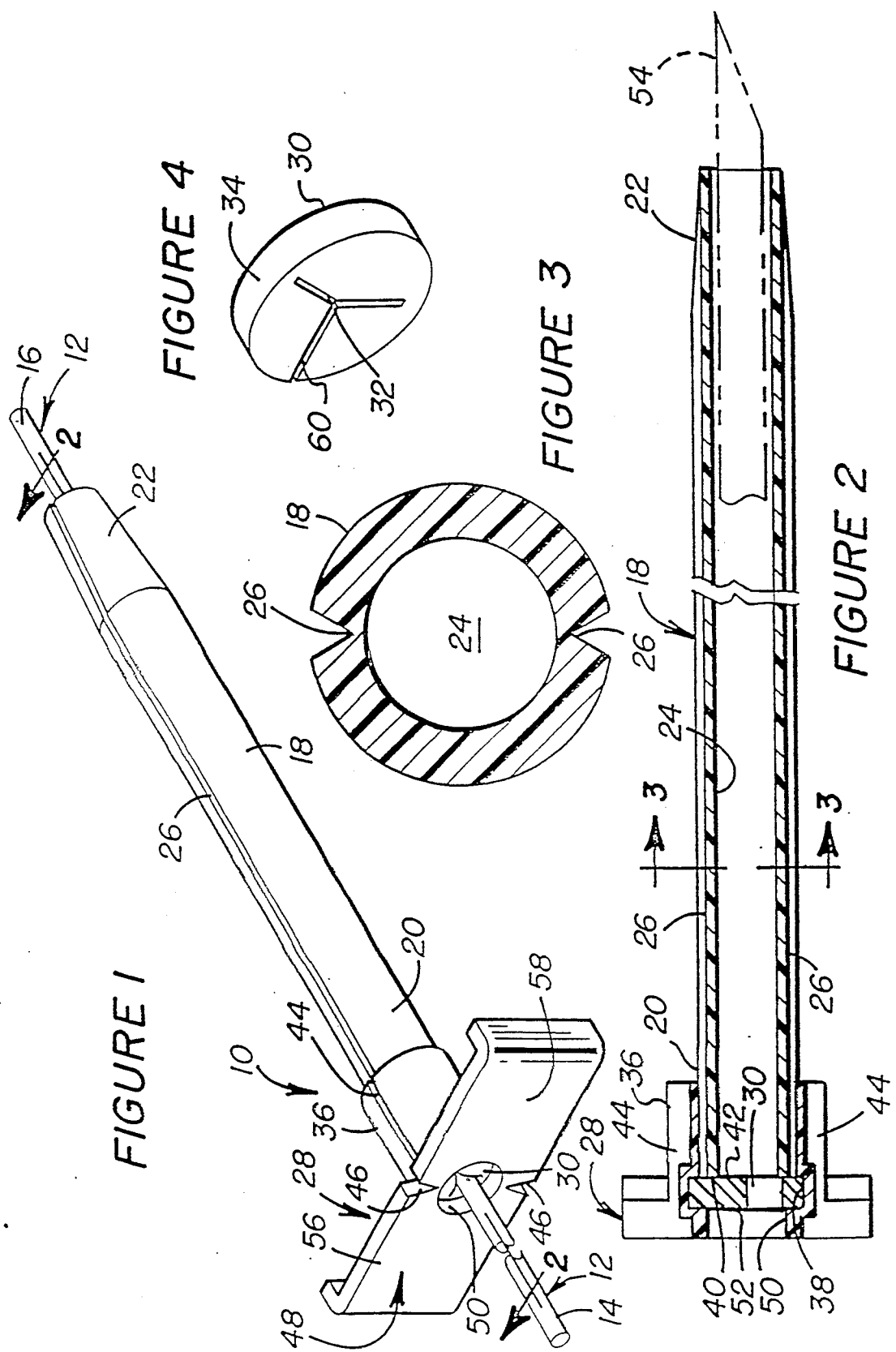

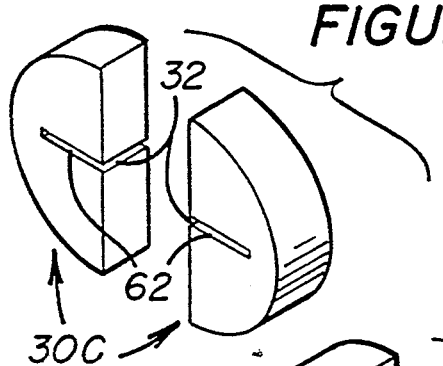
FIGURE 8
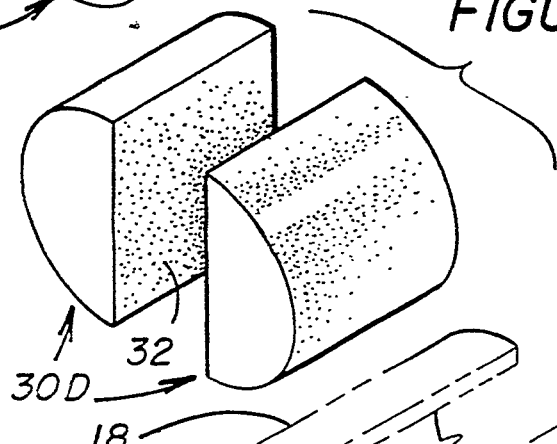
FIGURE 9
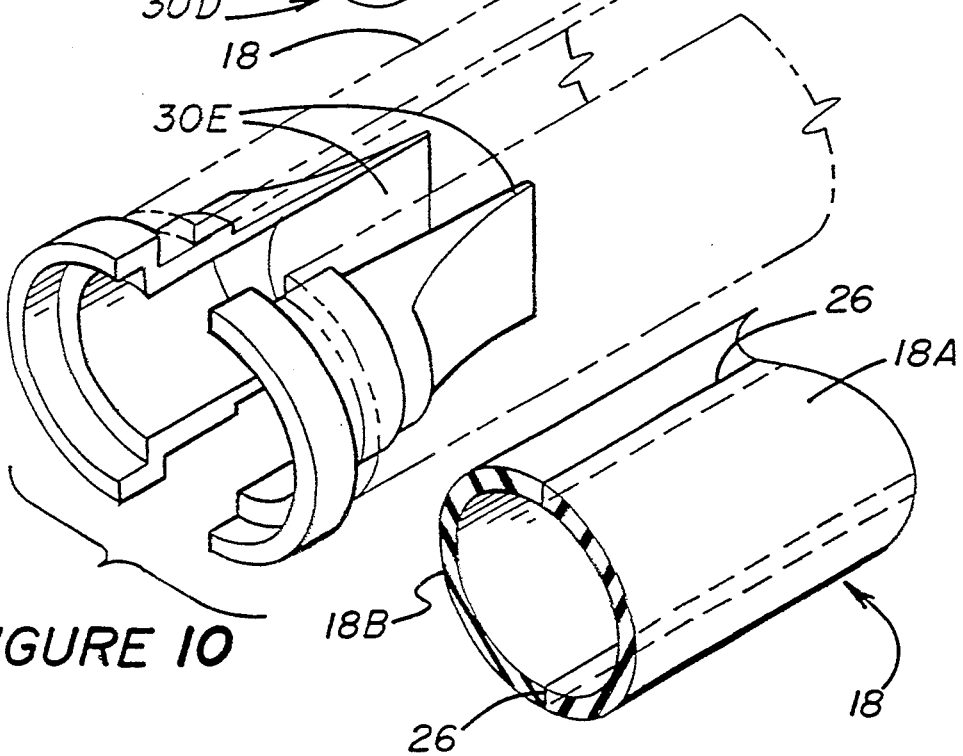
FIGURE 10
FIGURE 17

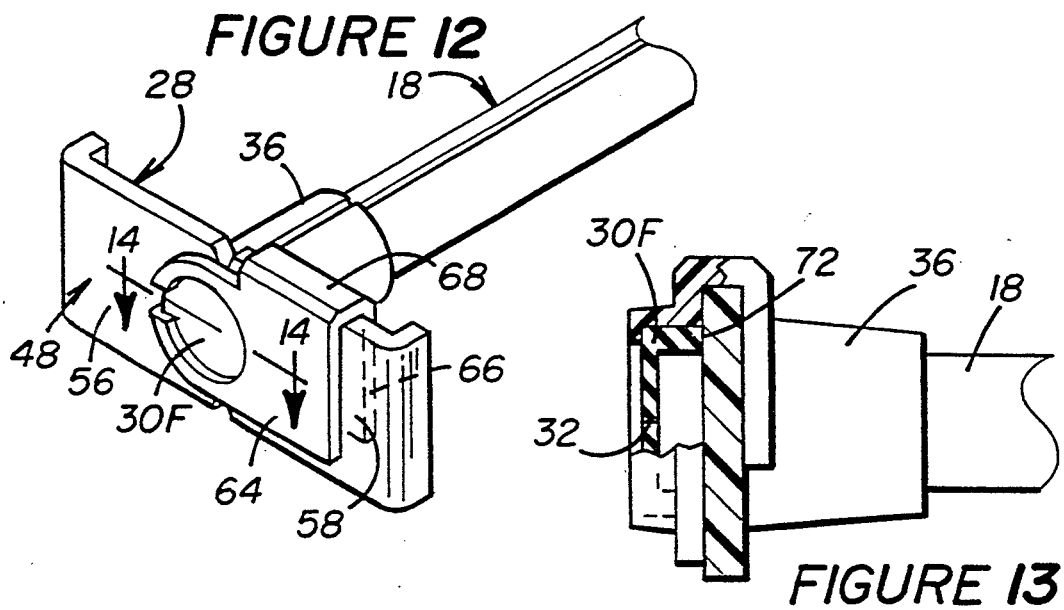
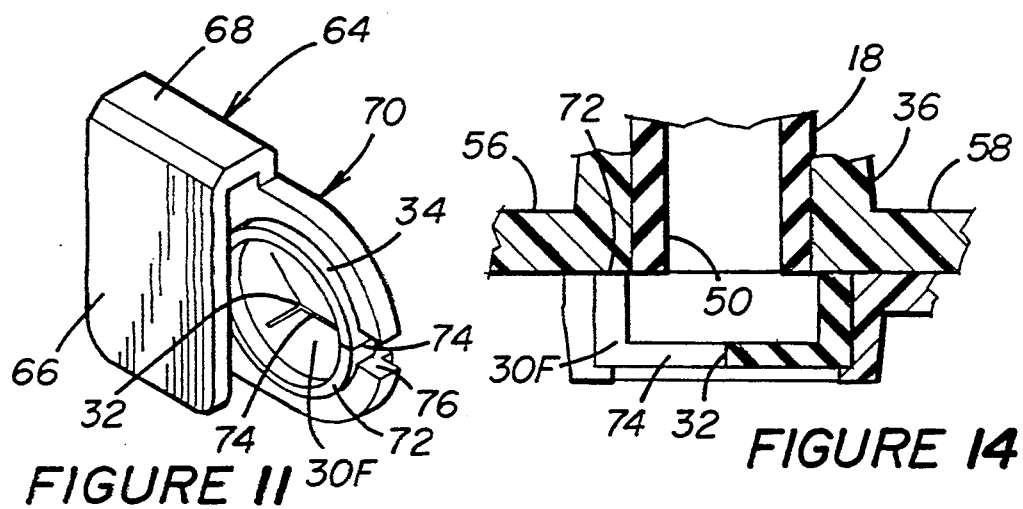
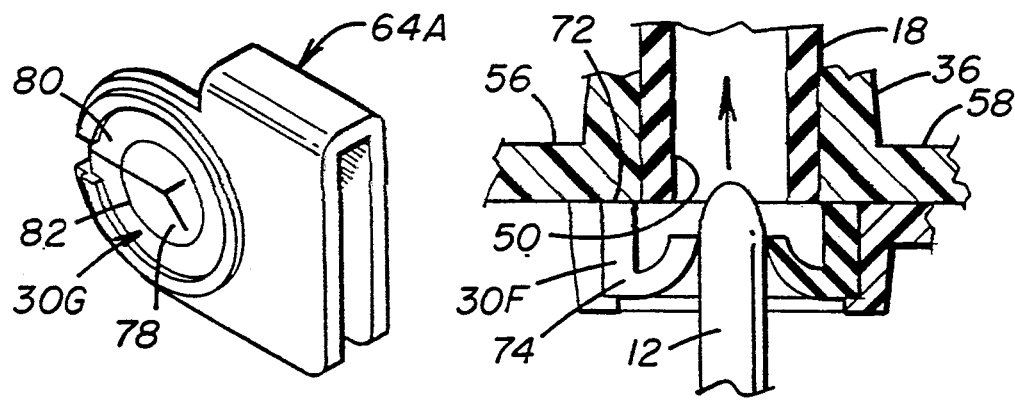

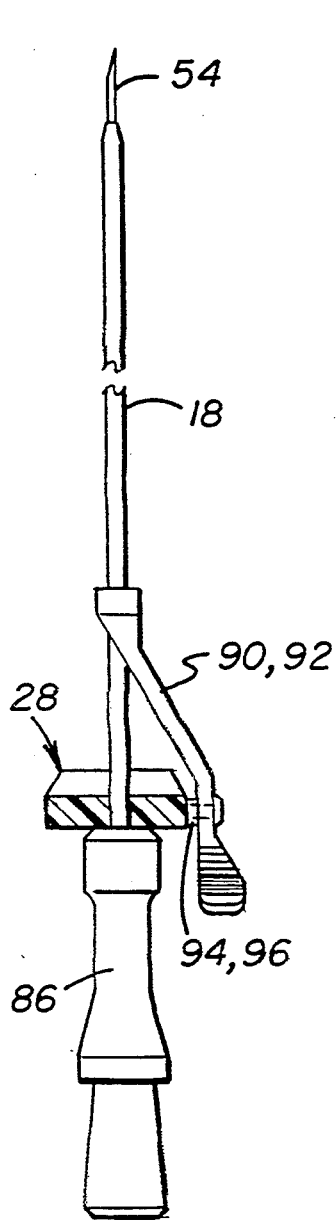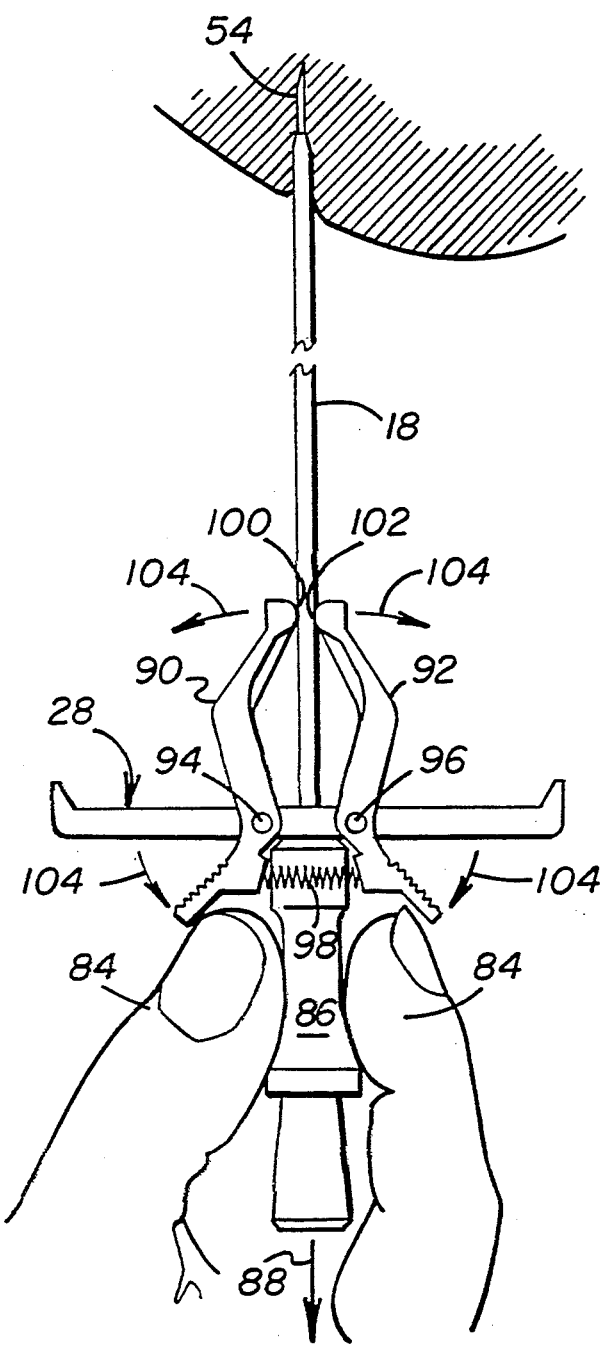
FIGURE 19
FIGURE 18

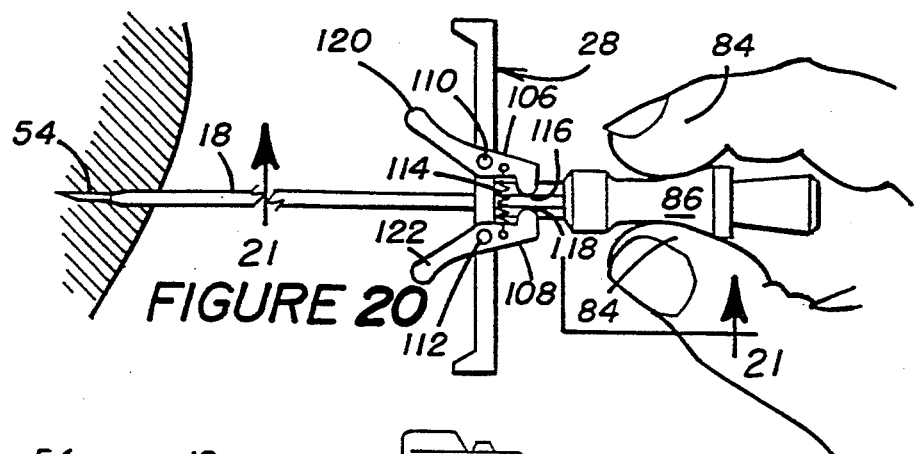
FIGURE 20
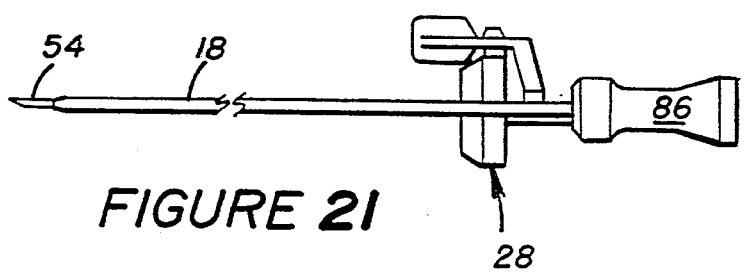
FIGURE 21
FIGURE 25
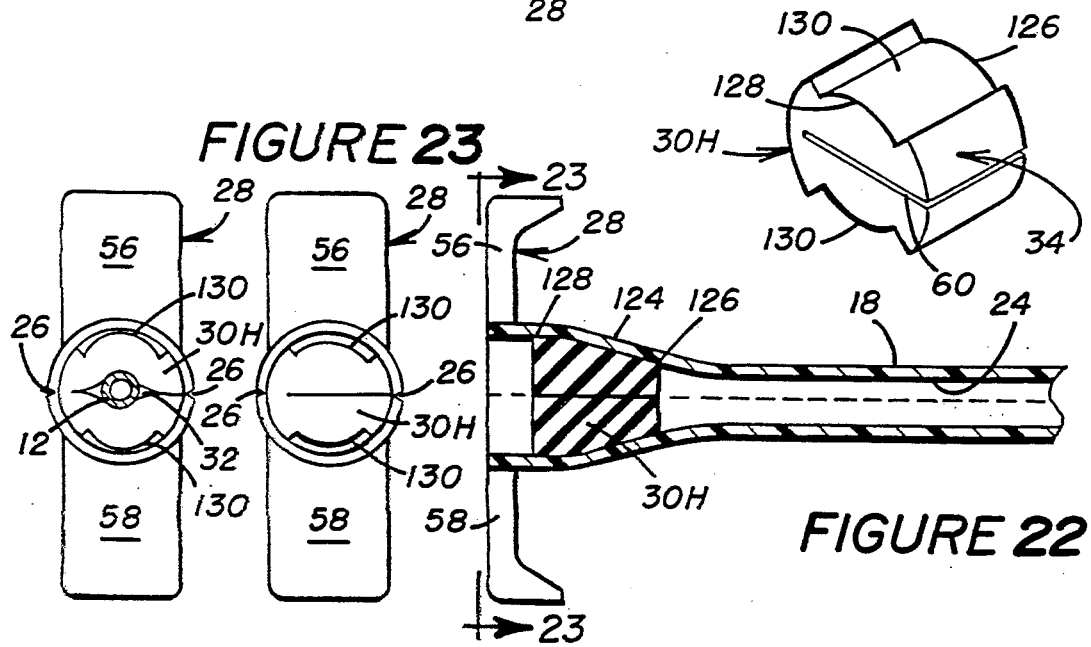
FIGURE 23
FIGURE 24
FIGURE 22
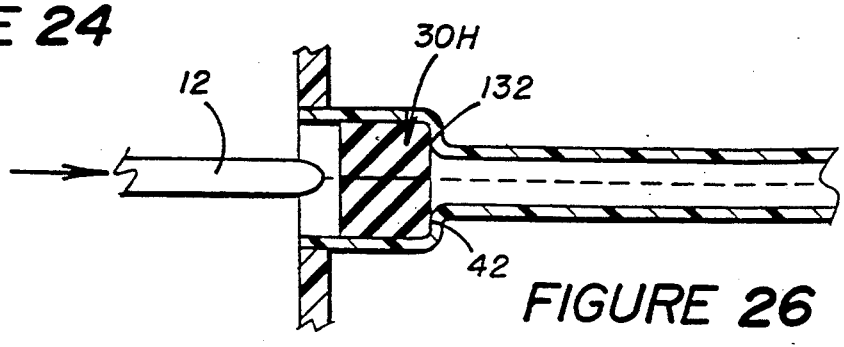
FIGURE 26

BLOODLESS SPLITTABLE INTRODUCER

TECHNICAL FIELD

The invention relates to an apparatus for the introduction of a longitudinally extending instrumentality such as a cannula or an electrode into a patient.

BACKGROUND OF THE INVENTION

Tubular inserters (introducer sheaths and needles) are available that can be used to puncture the skin and access body cavities (i.e., veins, arteries, the stomach, etc.). Catheters, electrodes or other devices can be threaded through the lumens of these devices into their required position.

Also commercially available are tubular inserters which can be removed from about the instrumentalities by splitting them. They can then be taken off of the instrumentalities through the split. Such tubular inserters are very useful but suffer from certain drawbacks. After insertion, they become an open pathway into and out of the body. Large amounts of blood loss and possible ingress of air or bacterial contamination are all possibilities. Physicians quite often cover the ends of these tubular inserters with their fingers to minimize these possibilities. This makes the feeding of the catheter or an electrode through the tubular inserters more difficult.

It would be desirable to provide a tubular inserter which did not suffer from the problems of blood escaping up its lumen and would minimize the risk of air or bacterial ingress when an instrumentality was inserted through it with the tubular inserter being of the splittable variety so that it could be removed after insertion of the instrumentality. The present invention addresses just this problem.

DISCLOSURE OF INVENTION

In accordance with an embodiment of the invention an apparatus is provided for facilitating substantially bloodless insertion into and withdrawal from a patient's body of a longitudinal member having a proximal end portion and having a distal end portion which is adapted to extend into the patient's body. The apparatus comprises a longitudinally extending sleeve having proximal and distal end portions and defining a lumen extending there along. Without limitation, the longitudinal member can be a needle or guide wire used for inserting the sleeve, a cannula, an electrode such as a pacemaker electrode, a diagnostic probe or the like. The longitudinal member is positionable along the lumen. The sleeve has a line extending longitudinally along it which is either split or is so weakened as to be splittable. As a result, the sleeve can be separated along the line for removal from about the longitudinal member without removal of its distal end portion from the patient. Valve means is provided for preventing blood flow through the lumen. Access means are present for allowing substantially bloodless insertion and withdrawal of the longitudinal member through the lumen.

In accordance with another aspect of the invention an apparatus is provided for the introduction into a patient of a longitudinal member having a distal end portion adapted to be extended into the patient. The apparatus comprises a longitudinal member having proximal and distal end portions. The distal end portion is adapted to extend into the patient. A longitudinally extending sleeve having proximal and distal end portions and defining a lumen extending there along also forms a part of the apparatus. The longitudinal member is positionable along the lumen. The sleeve has a line extending longitudinally along it which is either split or so weakened as to be splittable. In this manner the sleeve can be separated along the line for removal from about the longitudinal member without removing its distal end portion from the patient. A sealing structure is provided which has an opening through it through which the longitudinal member fits in substantially sealing relation. The sealing structure preferably includes a portion which is either split or is adapted to be split through to the opening. This allows the sealing structure to be removed from about the longitudinal member while the distal end portion of the longitudinal member remains extended into the patient. The sealing structure is attached so as to be in flow blocking relationship to the lumen.

In accordance with another embodiment of the present invention, an apparatus is provided for the introduction into a patient of a longitudinal member having proximal and distal end portions such that its distal end portion extends into the patient. The apparatus comprises a sealing structure having an opening through which the longitudinal member can fit in substantially sealing relation. The sealing structure includes a portion which is preferably either split or adapted to be split through to the opening. This allows the sealing structure to be removed from about the longitudinal member without removing its distal end portion from the patient. A longitudinally extended sleeve is provided having proximal and distal end portions and defining a lumen extending there along. The lumen is adapted to have the longitudinal member positioned there along. The sleeve has a line extending longitudinally along it which is either split or is so weakened as to be splittable so that the sleeve can be separated along the line for removal from about the longitudinal member. This allows the sleeve to be removed from about the longitudinal member without removing its distal end portion from the patient. The sealing structure is attached so as to block flow through the lumen.

In accordance with yet another embodiment of the invention, a method is set forth of inserting a longitudinally extending instrumentality such as a cannula, an electrode, a guide wire a diagnostic probe or the like into a patient. The longitudinally extending instrumentality has a proximal end portion which is adapted to extend out of the patient and a distal end portion which is adapted to be extended into the patient. The method comprises positioning a longitudinal member such as a needle or guide wire through (a) an opening in a sealing structure in such a manner that the longitudinal member is in substantially sealing relationship to the opening, the sealing structure including a portion which is either split or is adapted to be split through to the opening and (b) a longitudinally extending sleeve having proximal and distal end portions and defining a lumen extending there along, the lumen being adapted to have the longitudinal member positioned there along. The sleeve has a line extending longitudinally there along which is either split or is so weakened as to be splittable so that the sleeve can be separated along the line for removal from about the longitudinally extending instrumentality. Thus, the sleeve can be removed while the distal end portion of the longitudinally extending instrumentality is extended into the patient. The sealing structure is attached so as to block flow through the lumen. The inserting is sufficiently so that the distal end portion of the longitudinal member extends into the patient. The longitudinal member is removed through the opening. The longitudinally extending instrumentality is inserted through the opening, through the lumen and into the patient. The sealing structure and the sleeve are removed from about the instrumentality without removing the distal end portion of the instrumentality from the patient.

Another embodiment still of the present invention is in the nature of an adaptor comprising a sealing structure having an opening therethrough through which a longitudinal member can fit in substantially sealing relation. The adaptor further includes means for attaching it to a longitudinally extending sleeve having proximal and distal end portions and defining a lumen extending there along, the lumen being adapted to have the longitudinal member position there along. The sleeve has a line extending longitudinally along it which is either split or so weakened as to be splittable so that the sleeve can be separated along the line for removal from about the longitudinal member while the distal end portion of the longitudinal member is extended into the patient. Means are also provided for attaching the sealing structure to prevent flow through the lumen.

Another embodiment yet of the invention is a splittable sheath. The sheath comprises a tube having opposite ends and defining a lumen. The tube is formed of a plurality of sealed together longitudinally extending segments at least two of which abut one another to define a line extending from one end of the tube to the other. The two segments are made of different materials or of a single material which has been cold welded together. The materials and the construction are such that the line is sufficiently weak so as to be splittable through to allow removal of the sheath from about a longitudinal member which is positioned along the lumen.

The present invention provides a number of advantages over the prior art. The main advantage is, of course, that substantially bloodless insertion and removal of longitudinally extending medical instrumentalities can be carried out and, thereafter, the introducer or tubular inserter through which the instrumentalities are inserted can be removed. In accordance with an embodiment of the invention, the tubular inserter can itself be inserted in an over-the-needle method, the needle can be bloodlessly removed through the tubular inserter and a sealing structure and an instrumentality such as an electrode or a cannula can then be inserted through the sealing structure and the tubular inserter and into the patient's body, following which the tubular inserter and the sealing structure can be removed from about the cannula. To the extent that it may be desirable, the tubular inserter and the sealing structure can be left in place while one longitudinally extending instrumentality is substituted for another. For example, a probe can first be inserted and then removed and replaced with an electrode such as a pacemaker electrode or with a cannula. Once the more permanent instrumentality is in place, the tubular inserter can be split, as preferably also can the sealing structure, whereby only the final instrumentality, for example, the cannula, is left in place.

BRIEF DESCRIPTION OF THE DRAWING

FIG. 1 illustrates, in perspective, an embodiment of a bloodless splittable introducer in accordance with an embodiment of the present invention;

FIG. 2 illustrates, a sectional view along line 2—2 of FIG. 1;

FIG. 3 illustrates a sectional view of the splittable introducer along line 3—3 of FIG. 2;

FIG. 4 illustrates, in perspective, a view of a sealing structure useful in various embodiments of the present invention.

FIG. 8 illustrates, in perspective view, an embodiment of a sealing structure useful in accordance with various embodiments of the present invention;

FIG. 9 illustrates, in view similar to FIG. 8, another embodiment of a sealing structure useful in accordance various embodiments of the present invention;

FIG. 10 illustrates, in perspective and with the splittable introducer shown in phantom, an embodiment wherein a flap valve is used in place of a sealing structure;

FIG. 11 illustrates, in perspective, a sealing structure containing adaptor which can be attached to a splittable introducer to allow for bloodless operation;

FIG. 12 illustrates, in perspective view, the adaptor of FIG. 11 attached to a splittable introducer;

FIG. 13 is a partial section view of the embodiment of FIG. 12;

FIG. 14 is a partial view, in section, taken along the line 14—14 of FIG. 12;

FIG. 15 is a view similar to FIG. 14 but showing insertion of a member through the sealing structure opening;

FIG. 16 illustrates, in perspective view, an alternative adaptor to that shown in FIG. 16;

FIG. 17 illustrates, in sectioned partial perspective view, an alternate construction to that shown in FIG. 3 for providing a splittable introducer tubular inserter;

FIG. 18 illustrates, in plan view, an embodiment of the present invention wherein an external clamp is utilized to clamp the sleeve shut and thereby to provide bloodless operation;

FIG. 19 illustrates the embodiment of FIG. 18 in side view;

FIG. 20 illustrates, in plan view, another embodiment wherein an external clamp is utilized to provide bloodless operation;

FIG. 21 illustrates a side view of the embodiment of FIG. 20;

FIG. 22 illustrates, in top section partial view, an embodiment of the present invention wherein a deformable relatively thick sealing structure is held within a tapered tubular introducer;

FIG. 23 is a view taken along the line 23—23 of FIG. 22;

FIG. 24 is a view similar to FIG. 23 but wherein a cannula is being inserted through a slit in the sealing structure of the FIG. 23 embodiment;

FIG. 25 illustrates the sealing structure of FIGS. 22-24; and

FIG. 26 illustrates an embodiment wherein the introducer includes a shoulder to hold a relatively thick sealing structure in a view similar to FIG. 22 but with a cannula being about to enter the sealing structure.

BEST MODE FOR CARRYING OUT INVENTION

Figure 5:
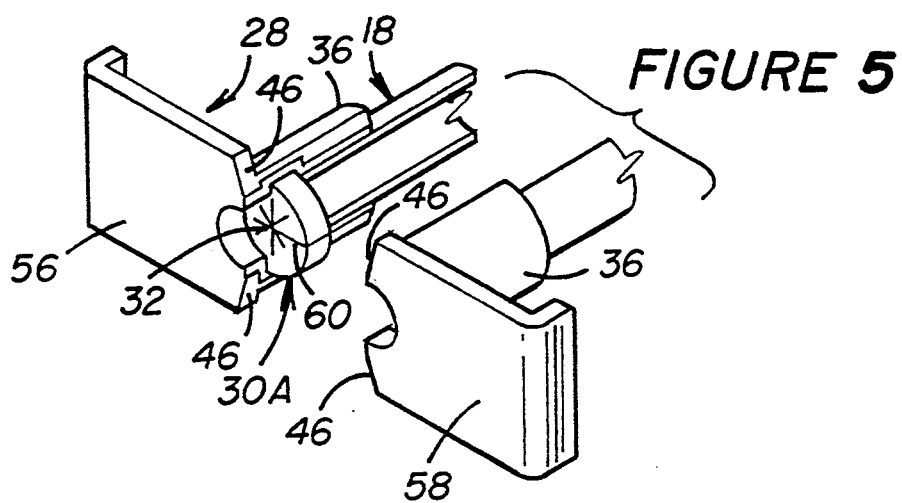
FIG. 5 illustrates, in partial perspective view, an embodiment generally as in FIG. 1 wherein the sealing structure is attached to one half of the splittable introducer.

An embodiment of an apparatus 10 is illustrated in FIGS. 1-4. The apparatus 10 is useful for facilitating substantially bloodless entrance to and egress from a patient's body. The apparatus 10 can accommodate a longitudinal member 12 having a proximal end portion 14 and a distal end portion 16. The distal end portion 16 of the longitudinal member is adapted to extend into the patient's body. The longitudinal member 12 can be in the nature of a needle, a cannula, an analytical probe, an electrode, or the like.

In accordance with the present invention, a longitudinally extending tubular introducer sleeve 18 is provided which has a proximal end portion 20 and a distal end portion 22. The longitudinally extending sleeve 18 defines a lumen 24 which extends along its length. The longitudinal member 12 is positionable along the lumen 24. The sleeve 18 has one or more lines 26 extending longitudinal along it, each of which is either split or is weakened so as to be splittable so that the sleeve 18 can be separated along the line 26 for removal from about the longitudinal member 12 while the distal end portion 16 of the longitudinal member 12 remains extended into the patient's body. In the particular embodiment illustrated in FIGS. 1, 2 and 3, the line 26 is in the nature of an indentation into the sleeve 18 and there are two such lines 26 separated from one another by 180°. One of the lines 26 can be split all the way through the sleeve 18 without causing any significant blood leakage problems, if desired, since the line 26 would normally be bias closed in such a situation due to the properties of the sleeve material which would normally be plastic. It is even possible in the case of a very stiff sleeve 18, for example, a sleeve 18 which is formulated of metal, for both of the lines 26 to be split all the way through since a sleeve holder 28, seen in FIG. 1, would then hold the two separated sides of the sleeve 18 together.

In accordance with the present invention, a sealing structure 30 of a biased shut configuration, for example, formulated of a deformable, generally elastomeric material or being biased shut by a spring or spring-like force, is provided having an opening 32 therethrough or formable therethrough and through which the longitudinal member 12 fits in substantially sealing relation. Because of the deformable, generally elastomeric, nature of the sealing member 30 of the embodiments which utilize such a deformable member, the opening 32 is self sealing in that it seals on removal of the longitudinal member 12. The sealing structure 30 is preferably adapted to be split through to the opening 32 to allow the sealing structure 30 to be removed from about the longitudinal member 12 while the distal end portion 16 of the longitudinal member 12 remains extended into the patient's body. This can be accomplished by an actual split through to the periphery 34 or by having a weakened portion which can be readily split through by the user.

The sealing structure 30 is attached in sealing relationship to the lumen 24 in any of a number of ways as are described herein. While it is preferred that the sealing structure 30 be adapted to be split through to the opening 32 to allow it to be removed from about the longitudinal member 12, it is also contemplated that the sealing structure 30 not be split through from its periphery 34 to the opening 32 in which case the sealing structure can simply remain about the longitudinal member 12 after the sleeve 18 is split and removed from about the longitudinal member 12.

The sealing structure 30 is attached in sealing relation to the lumen 24 making use of the sleeve holder 28. This can be accomplished in a number of ways as will be discussed below with respect to various embodiments of the invention. In the embodiments shown in FIGS. 1-4, the longitudinally extending sleeve 18 is bonded to the sleeve holder 28 and more particularly, to a distal tubular portion 36 thereof as seen most clearly in FIG. 2. The sealing structure 30, which in the embodiments of FIGS. 1-4 is in the nature of an elastomeric disk, is also held by the sleeve holder 28 as illustrated. In the particular embodiment shown in FIG. 2, the sealing structure 30 is held, for example adhesively attached or simply interference fit, in an undercut 38. The proximal end 30 of the proximal end portion 20 of the sleeve 18 abuts against a distal facing side 42 of the sealing structure 30. Thus, any blood leakage is precluded.

The sleeve holder 28 also serves the important purpose of motivating splitting of the longitudinally extending sleeve 18. As will be noted by reference to FIG. 1 and 2, the tubular portion 36 of the sleeve holder 28 is itself split along a line or lines 44, which lines 44 are in alignment with the lines 26 in the sleeve 18. Furthermore, deep notches 46 are provided in a table portion 48 of the sleeve holder 28. As will be noted, an opening 50 in the table portion 48 of the sleeve holder 28 provides access to a proximally facing side 52 of the sealing structure 30. In this manner the longitudinal member 12 can be contacted with the opening 32 in the sealing structure 30 and can then pass through the sleeve 18 to the position illustrated in FIG. 1.

FIG. 2 shows one type of longitudinal member 12, namely a needle 54, in phantom within the sleeve 18. For insertion in a person's body, the needle 54 is placed within the sleeve 18, generally as shown in FIG. 2, and the needle 54, along with at least the distal end portion 22 of the sleeve 18, is passed into the patient's body. The needle 54 is then removed through the opening 32 in the sealing structure 30 and another longitudinal member 12, such as a cannula, a dilator or an electrode is passed through the opening 32 in a distal direction until it extends a desired distance into the patient's body.

The sleeve holder 28 also serves an additional purpose. As will be noted, the table portion 48 of the sleeve 28 is in the nature of two wings 56 and 58. Once the longitudinal member 12 has been properly positioned within the patient's body, the medical practitioner can withdraw the sleeve 18 from the patient's body while it remains about the longitudinal member 12. Thereafter, the medical practitioner can grasp the wings 56 and 58 and snap the table 48 in half at the lines 46 and 44. Since the proximal end portion 20 of the sleeve 18 is attached, e.g., adhesively or by welding, to the two portion 36 of the sleeve holder 28, and since the slots 26 are present in the sleeve 18, the sleeve 18 is split along the lines 26 following splitting of the sleeve holder 28 along the lines 46 and 44. If the sealing structure 30 includes a slot 60 which extends to periphery 34 of the sealing structure 30, the sealing structure 30 can be removed from about the longitudinal member 12 via the slot 60. However, at times the slot 60 may not be present or may not extend all the way to the periphery 34 of the sealing structure 30. In such an instance, the sealing structure 30 will not be attached to the sleeve holder 28 and will remain about the longitudinal member 12.

It should be noted that the apparatus 10 provides essentially bloodless entrance to and egress from a patient's body. When the needle 54 is in place and is inserted into the patient's body (to accomplish insertion of the sleeve 18), its periphery is sealed to the opening 32 whereby no significant blood leakage can occur. On removal of the needle 54, the sealing structure 30 seals as the opening 32 closes whereby, once again, substantially no bleeding occurs. When the longitudinal member 12 is inserted through the opening 32 it, likewise, seals to the opening 32 whereby no bleeding occurs.

FIG. 5 illustrates a split apart sealing structure embodiment wherein a sealing structure 30A, of similar material but with a slightly different geometry for its opening 32 than the sealing structure 30, is shown in a sleeve holder 28 which has been split apart for purposes of illustration. As will be noted, the sealing structure 30A is attached to the portion of the sleeve holder 28 which includes the wing 56 and approximately one half of the tubular inserter portion 36. The other half of the sealing structure 30 is not attached to the portion of the sleeve holder 28 which includes the wing 58 and the other half of the tubular portion 36. In such an embodiment, the slit 60 is positioned for easy removal of the longitudinal member 12.

Figure 6:
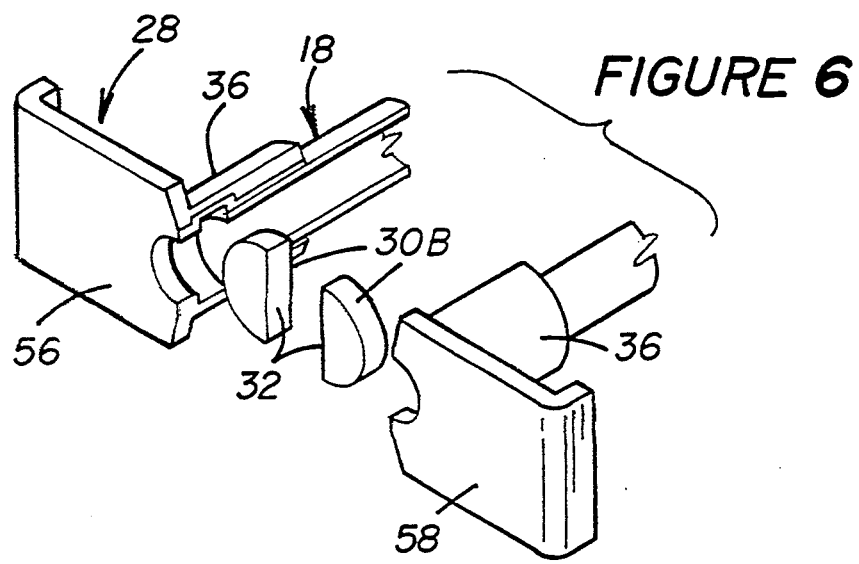
FIG. 6 illustrates, in a view similar to FIG. 5, an embodiment wherein a two-piece sealing structure is utilized which is not attached to either side of the splittable introducer.

FIG. 6 shows an embodiment wherein the sealing structure 30B is in the form of two semicircular, generally elastomeric, members, each of which is free from connection with the portions of the sleeve holder 28 which are attached to the respective wings 56 and 58. The opening 32 is defined by the facing abutting surfaces of the two semicircular elastomeric members which together comprise the sealing structure 30.

Figure 7:
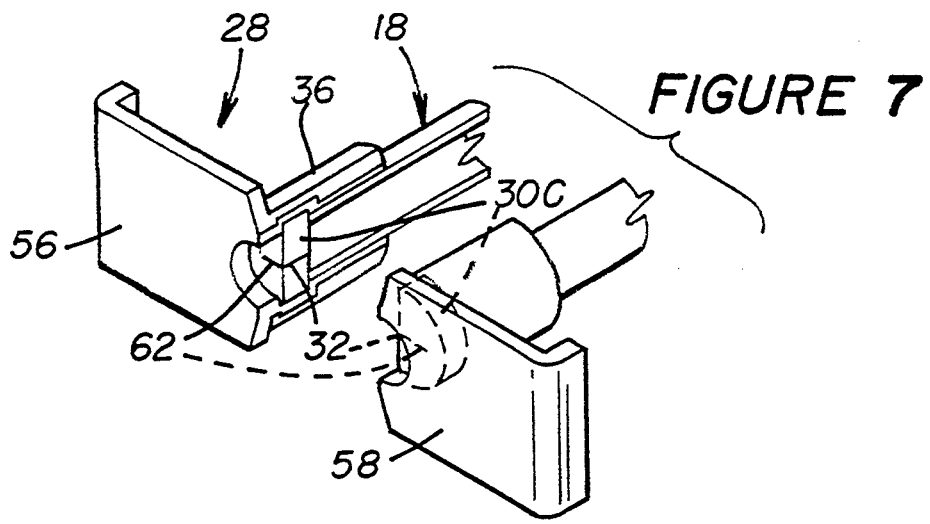
FIG. 7 illustrates, in a view similar to FIG. 5, an embodiment wherein a split sealing structure is utilized with each half of the sealing structure being attached to one half of the splittable introducer.

FIG. 7 illustrates an embodiment wherein the sealing structure 30C is in the nature of two semicircular parts, one attached to the portion of the sleeve holder 28 which is attached to the wing 56 and the other being similarly attached to the portion of the sleeve holder 28 which is attached to the wing 58. On separation of the wings 56 and 58, and of the sleeve 18, all as shown in FIG. 7, the longitudinal member 12 is free from both the sealing structure 30 and the sleeve 18. Note that the slots 62 shown in FIG. 7 can be omitted, or such slots can added to the embodiment of FIG. 6. Basically, the presence of the slots 62 is to aid in providing a good seal about the longitudinal member 12. Note also that the portions of the sealing structure 30C are each attached to a respective portion of the sleeve holder 28 which has either the wing 56 or the wing 58. FIG. 8 is a more detailed and somewhat clearer drawing of the sealing structure 33.

FIG. 9 is a drawing of a sealing structure 30D, which is much like that shown in FIG. 6 but which is considerably more extensive along the direction of the longitudinal extending sleeve 18 whereby a better seal can be provided to the longitudinal member 12. The material of the sealing structure 30D is suitably more compressible than that of embodiments which utilize a less thick sealing structure.

FIG. 10 illustrates an embodiment wherein a sealing structure 30E is utilized which is in the nature of a flap valve made of an elastomeric material. The sleeve 18 is shown in phantom and in the position where it has been split. The sleeve holder 28 has been omitted from FIG. 4 for clarity of illustration.

FIGS. 11-15 illustrate an embodiment of the present invention wherein an adaptor 64 can be attached to a pre-existing sleeve holder 28 which does not have a sealing structure 30. The adaptor 64 is in the nature of a clip which includes a leg 66 which is adapted to fit against a distal side of one of the wings 56, 58, a bridge portion 68 and a sealing structure mounting structure 70 which fits sealingly around the opening 50 in the table portion 48 of the sleeve holder 28. In the embodiment of FIGS. 11-15, the sealing structure 30F is cup shaped and the cup has a base 72, the cup shaped sealing structure 30F being abutted against the table 48 to provide a sealing relationship about the hole 50. The resiliency of the sealing structure 30F, along with the resiliency of the adaptor 64 provides a snap fit engagement of the adapter 64 over the wing 58 as shown in FIG. 12 with the required sealing at 72. Note that the sealing structure 30 includes a slit 74 which extends to the periphery 34 of the sealing structure 30F. Note also that the adaptor 64 defines a gap 76 such that the longitudinal member 12 can be removed through the slit 74 and through the gap 76. FIGS. 14 and 15 illustrate operation of the sealing structure 30F with FIG. 14 showing the sealing structure 30F without a longitudinal member 12 projecting through the opening 32 and with FIG. 15 showing a longitudinal member 12 extending through the opening 32. The slit 74 is horizontal in FIG. 14, but for illustrative purposes, the slit 74 is vertical in FIG. 15 to show how the longitudinal member 12 extends through the opening.

FIG. 16 illustrates an adaptor 64A, which is like the adaptor 64 shown in FIG. 11. However, the sealing structure 30G is in the nature of a pair of elastomeric members 78 and 80 with the elastomeric member 78 being split to its periphery 34 and with a circular hole 82 being present in the elastomeric member 80, the hole 82 being adapted to seal to the outer periphery of a longitudinal member. The elastomeric members 78 and 80 are located one behind the other and abut one another whereby when the slits 74 are opened by a longitudinal member such as a cannula being pushed therethrough, the hole 82 seals to the periphery of the longitudinal member thus assuring substantially bloodless insertion of the longitudinal member.

Figure 16A:
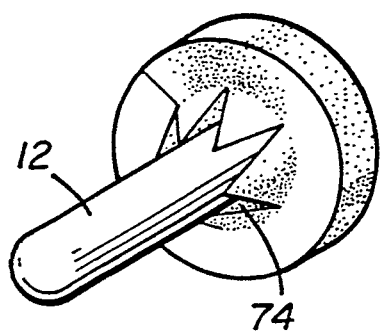
FIGS. 16a–16c provide an exploded view of the alternative adaptor shown in FIG. 16.
Figure 16B:
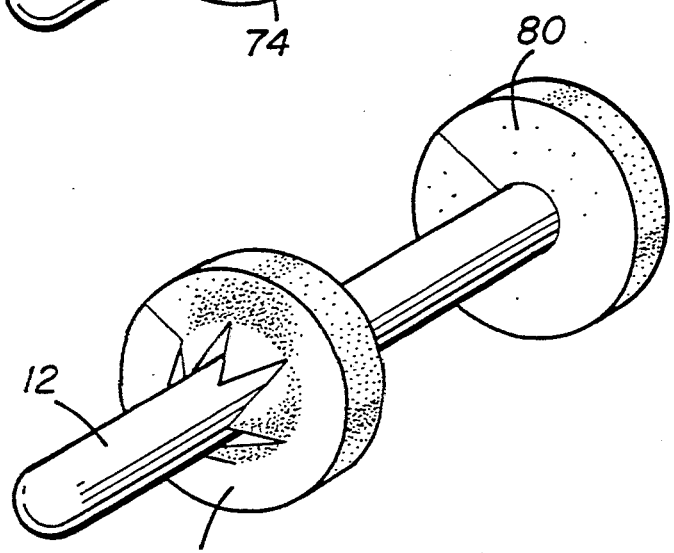
Figure 16C:
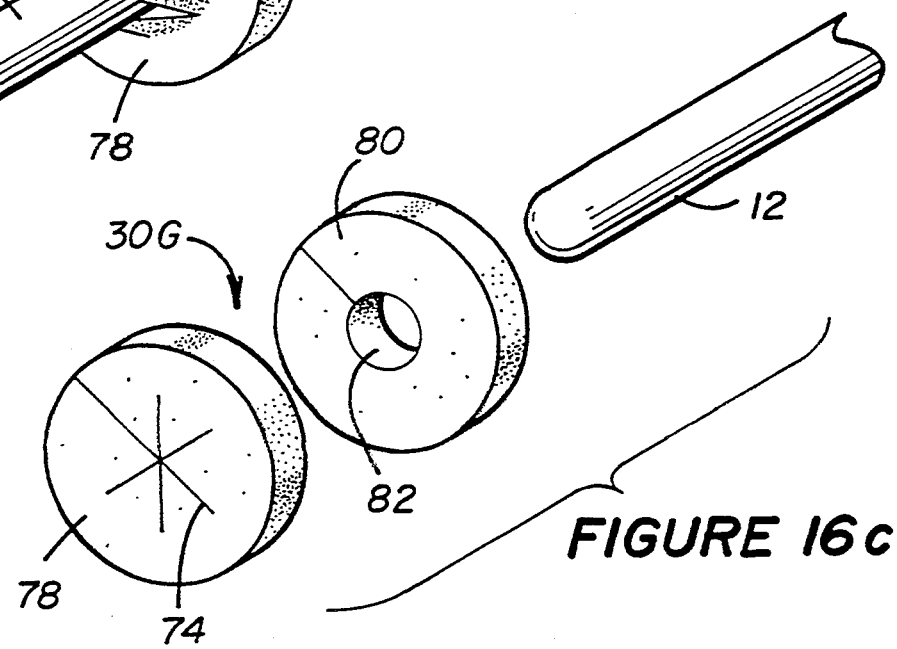

FIG. 16a illustrates a longitudinal member 12 being pushed through the slit 74 of the sealing structure 30g. FIGS. 16b and 16c illustrate the pair of elastic members 78 and 80. During introduction of a longitudinal member 12, the slit 74 may allow some leakage, but forms a tight seal upon removal of the longitudinal member 12. By including the dual septum (78 and 80), the elastic member 80 provides sealing during feeding of the longitudinal member 12, and the elastic member 78 provides sealing upon removal of the longitudinal member 12. Accordingly, a hermetic or tight seal is provided during all stages of insertion and removal of a longitudinal member 12.

FIG. 17 shows an embodiment of the present invention wherein the sleeve 18 is in the nature of two facing semi cylinders 18A and 18B which are formed of different materials and which are sealed together to form the weakened lines 26. By correct choosing of the materials and of the method of sealing the two semicylinders 18A and 18B together, one can arrange that the lines 26 are weakened to a desired extent. The longitudinally extending sleeve 18' of FIG. 17 can be used in the same manner as can the longitudinally extending sleeve 18 shown in the other figures.

FIG. 18 and 19 illustrates still another embodiment of the present invention. FIG. 18 illustrates a needle 54 projecting through the sleeve 18 which is held by the sleeve holder 28. Fingers 84 are shown grasping a needle hub 86 in position to remove it in the direction shown by arrow 88 from the sleeve 18. When this occurs, a pair of arms 90, 92 pivoted respectively at pivots 94 and 96 to the sleeve holder 28, are impelled by spring 98 to provide pressure between points 100 and 102 against the outer surface of the sleeve 18. This provides a pinching motion whereby the sleeve 18 is pinched off and closed to flow on removal of the needle 54 past the points 100 and 102. When it is time to advance a longitudinal member 12 through the sleeve 18, the user places the fingers 84 on the roughened portions of the levers 90 and 92 whereby forcing the points 100 and 102 apart and allowing insertion of the longitudinal member 12. In the embodiment of FIG. 15, therefore, the use of a sealing structure 30 is unnecessary. FIG. 19 is a side view, partially in section, which better shows the pivotal mounting of the levers 90 and 92. The arrows 104 in FIG. 18 show the movement of the levers 90 and 92 when the fingers 84 are utilized to compress the spring 98.

FIG. 20 and 21 illustrate an embodiment which is similar to that of FIGS. 18 and 19 in that a sealing structure 30 is not utilized. In the embodiment of FIGS. 20 and 21 the levers 106, 108 are mounted pivotally respectively at 110, 112. The spring 114 biases the contact points 116, 118 towards one another. Also, the sleeve 18 extends through but is attached to the sleeve holder 28. When the needle 54 is removed by moving the needle hub 86 utilizing the fingers 84, the pressure points 116, 118 are pulled together by the spring 114 sufficiently to close off the sleeve 18. When it is desired to re-open the sleeve 18 in order to insert a longitudinal member 112, the finger 84 can be utilized on the ends 120, 122 of the levers 106, 108 so as to force the pressure points 116, 118 apart as the longitudinal member 12 is advanced through the lumen 24 of the sleeve 18.

FIG. 22-25 illustrates still another embodiment of the present invention. In the embodiment of these figures, the sleeve 18 has a tapered section 124 which entraps an elastomeric sealing structure 30H. The fit is tight enough at a distal end 126 of the sealing structure 30H so as to provide a tight seal. Towards a proximal end 128 of the sealing structure 30H, the seal is not quite as tight due to the presence of one or more cut-outs 130 along the radial outer periphery 34 of the sealing structure 30H. FIG. 23 illustrates the sealing structure 30H in place and in sealing relationship with the lumen 24 of the sleeve 18 due to the tight fit at the distal end 126 of the sealing structure 30H. FIG. 24 shows a longitudinal member 12 being inserted through the opening 32 in the sealing structure 30H and also demonstrates the flexing at the periphery 34 of the sealing structure 30H which occurs to allow relatively easy insertion of the longitudinal member 12.

FIG. 26 shows another embodiment which can utilize the sealing structure 30H. In the embodiment of FIG. 26, the tapered section 24 of FIG. 22 is replaced by a shoulder 132 which abuts against the distal end 42 of the sealing structure 30H. In this manner, the flexing shown in FIG. 23 and 24 can occur while good sealing results since the shoulder 132 extends more than the depth of the undercuts 130.

The invention also provides a method of inserting a longitudinal member 12 into a patient's body. The longitudinal member 12 is inserted through the opening 32 in a sealing structure 30 in such a manner that the longitudinal member 12 is in substantial sealing relation to the opening 30. The longitudinal extending sleeve 18 has a line 26 extending along its length which is either split or so weakened as to be splittable so that the sleeve can be separated along the line for removal from about the longitudinal member. The sealing structure is attached in sealing relationship to the lumen of the sleeve. The longitudinal member 12 is removed through the opening 32. Another longitudinal member 12 is inserted through the opening 32 until the other longitudinal member 12 extends into the patient's body. The sleeve is removed from about the other longitudinal member while leaving the other longitudinal member with its distal end portion extending into the patient's body.

Industrial Applicability

The present invention provides an apparatus and method for bloodless insertion and removal of needles, dilators, cannulae, electrodes and the like from a patient's body. A sleeve 18 can be split away from about the longitudinal member 12 and can be removed therefrom. In accordance with certain embodiments of the present invention, a sealing structure 30 can likewise be removed without removing the longitudinal member 12.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. An apparatus for facilitating substantially bloodless insertion into and withdrawal from a patient's body of a longitudinal member having a proximal end portion and having a distal end portion which is adapted to extend into the patient's body, comprising:

a longitudinally extending sleeve having proximal and distal end portions and defining a lumen extending therealong, the longitudinal member being positionable along the lumen, the sleeve having a line extending longitudinally therealong which is either split or is so weakened as to be splittable so that the sleeve can be separated along the line for removal from about the longitudinal member while the distal end portion of the longitudinal member remains extended into the patient;

a sleeve holder to which the proximal end portion of the sleeve is attached, the sleeve holder being so weakened in corresponding relation to the line on the sleeve so that the sleeve can be separated along the line for removal from about the longitudinal member while the distal end portion of the longitudinal member remains extended into the patient; and a sealing structure held by the sleeve holder so as to be in sealing relationship to the lumen, the sealing structure including 1) a self sealing opening and 2) a substantially circular opening located proximally of the self sealing opening and being substantially coaxial therewith, the circular opening having a diameter which is equal to or less than an external diameter of the longitudinal member so as to form a sliding seal to prevent significant blood loss during insertion and withdrawal of the longitudinal member through the lumen.

2. An apparatus as set forth in claim 1, wherein the sealing structure is adapted to be split through to the opening to allow the sealing structure to be removed from about the longitudinal member while the distal end portion of the longitudinal member remains extended into the patient.

3. An apparatus as set forth in claim 1, wherein the sealing structure is mounted to an adaptor and further including:

attachment means for attaching the adaptor to the sleeve holder.

* * * * *